United States Patent [19]
Chodnekar et al.

[11] 3,983,247
[45] Sept. 28, 1976

[54] 2,4-DODECADIENOIC ACID ESTERS AND USE FOR INSECTICIDES

[75] Inventors: Madhukar Subraya Chodnekar, Seltisberg; Ulrich Schwieter, Reinach; Peter Loeliger, Pfaffhausen; Albert Pfiffner, Bulach; Milos Suchy; René Zurflüh, both of Pfaffhausen, all of Switzerland

[73] Assignee: Hoffmann-La Roche Inc., Nutley, N.J.

[22] Filed: Mar. 18, 1975

[21] Appl. No.: 559,619

[30] Foreign Application Priority Data
Mar. 22, 1974 Switzerland............... 4037/74

[52] U.S. Cl............ 424/312; 424/DIG. 12; 260/410.9 R; 260/DIG. 44
[51] Int. Cl.$^2$............ C11C 3/02; A01N 9/24; A61K 31/23
[58] Field of Search............ 260/410.9 R, DIG. 44; 424/312, DIG. 12

[56] References Cited
UNITED STATES PATENTS

| | | | |
|---|---|---|---|
| 3,712,922 | 1/1973 | Henrick | 260/410.9 R |
| 3,773,793 | 11/1973 | Henrick | 260/410.9 R |
| 3,801,608 | 4/1974 | Henrick | 260/410.9 R |
| 3,887,592 | 6/1975 | Henrick | 260/410.9 R |
| 3,904,662 | 9/1975 | Henrick | 260/410.9 R |

*Primary Examiner*—Patrick P. Garvin
*Assistant Examiner*—John F. Niebling
*Attorney, Agent, or Firm*—Samuel L. Welt; Bernard S. Leon; Richard A. Gaither

[57] ABSTRACT

The present invention relates to polyene compounds, a process for their preparation, pesticidal compositions containing same, and a method of providing a locus free from pests using said pesticides, alone or in composition.

16 Claims, No Drawings

2,4-DODECADIENOIC ACID ESTERS AND USE FOR INSECTICIDES

SUMMARY OF THE INVENTION

The polyene compounds provided by the present invention have the following formula:

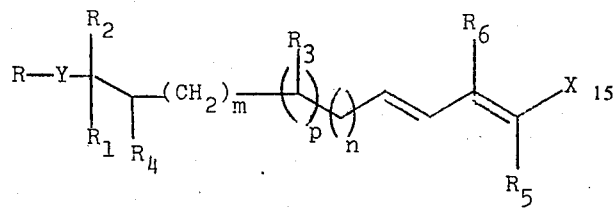

I wherein R is lower alkenyl, lower alkynyl or a cyclopropylmethyl group, $R_1$, $R_2$, $R_3$ and $R_6$ are each hydrogen or lower alkyl, $R_4$ and $R_5$ are each hydrogen or a methyl group, Y is oxygen or sulphur, X is a group selected from the following —$COOR_7$, —$CH_2OR_7$ or —$COSR_7$, in which $R_7$ is lower alkyl, lower alkenyl, lower alkynyl or a cyclopropylmethyl group; n and p are zero or 1 and m is an integer from zero to 2, inclusive.

According to the process of the instant invention, the polyene compounds of formula I may be prepared by a. reacting a carbonyl compound of the formula:

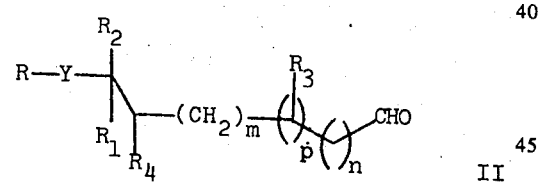

II wherein R, $R_1$, $R_2$, $R_3$, $R_4$, Y, m, n and p are as defined above;
with a phosphine oxide of the formula:

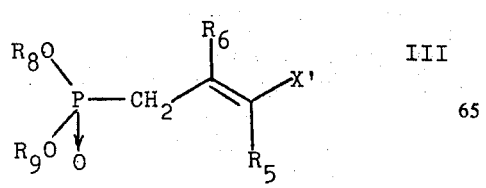

III wherein X′ is —$COOR_7$ in which $R_7$ is as defined above, $R_8$ and $R_9$ are each lower alkyl or a substituted or unsubstituted aryl group; $R_5$ and $R_6$ are as defined above;
or b. reacting a carbonyl compound of formula II with a phosphorane of the formula:

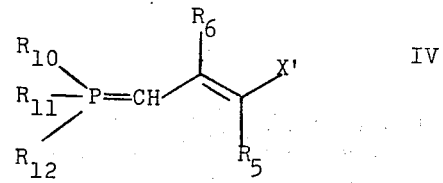

IV wherein X′, $R_5$ and $R_6$ are as defined above; $R_{10}$ and $R_{11}$ and $R_{12}$ are each aryl or dialkylamino;
or c. reacting a carbonyl compound of the formula:

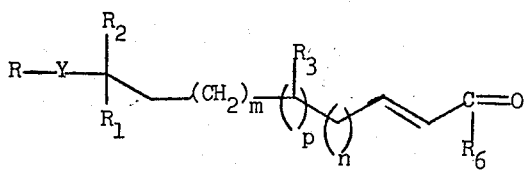

V wherein R, $R_1$, $R_2$, $R_3$, $R_4$, $R_6$, Y, n, m and p are as defined above;
with a phosphine oxide of the formula:

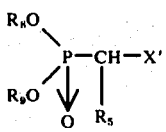

VI wherein $R_5$, $R_8$, $R_9$ and X′ are as defined above; or d. reacting a carbonyl compound of V with a phosphorane of the formula:

VII wherein $R_{10}$, $R_{11}$, $R_{12}$ and X′ are as defined above; or e. reacting a compound of the formula:

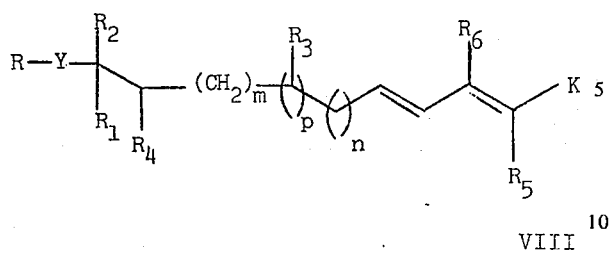

VIII wherein R, $R_1$, $R_2$, $R_3$, $R_4$, $R_5$, $R_6$, $R_7$, Y, m, n and p are as defined above; K is chlorine, bromine, iodine atom or tosyloxy;
with a compound of the formula:

$$J-R_7 \qquad \qquad IX$$

wherein $R_7$ is as defined above; J is chlorine, bromine, iodine or tosyloxy;
with the proviso that when either of K or J is chlorine, bromine or tosyloxy, the other is —OM in which M represents an alkali metal or alkaline earth metal;
or f. reacting a carbonyl compound of formula II with a compound of the formula:

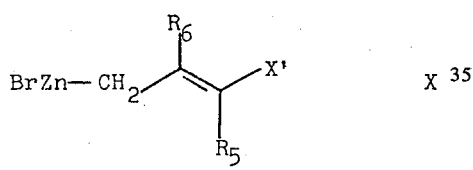

X wherein $R_5$, $R_6$ and X' are previously defined; Zn is zinc and Br is bromine;
and dehydrating the resulting compound of the formula:

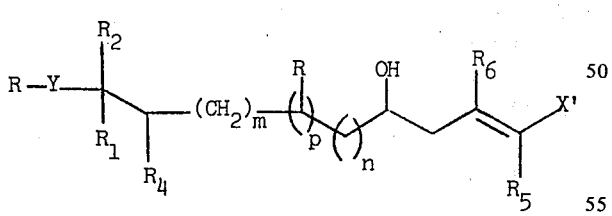

XI wherein R, $R_1$, $R_2$, $R_3$, $R_4$, $R_5$, $R_6$, X', Y, m, n and p are as previously defined;
or g. reacting a carbonyl compound of formula V with a compound of the formula:

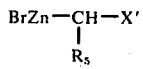

XII wherein $R_5$, X', Zn and Br are as previously defined; and dehydrating the resulting compound of the formula:

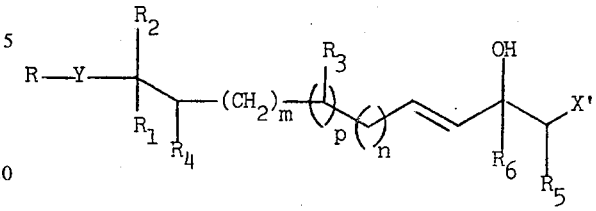

XIII wherein R, $R_1$, $R_2$, $R_3$, $R_4$, $R_5$, $R_6$, X', Y, m, n and p are as previously defined;
or h. converting an acid of the formula:

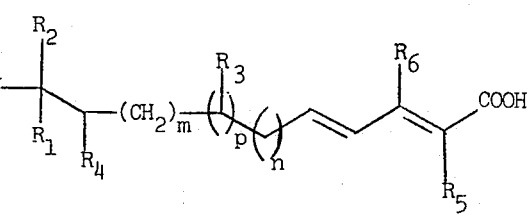

XIV wherein R, $R_1$, $R_2$, $R_3$, $R_4$, $R_5$, $R_6$, Y, n, m and p are as previously defined;
or its corresponding acid halide into a lower alkyl, lower alkenyl, lower alkynyl or cyclopropylmethyl ester according to known procedures, or i. reacting a polyene compound of formula I in which Y is oxygen or sulphur and R is hydrogen with a compound of the formula:

$$R_{13}-Z \qquad \qquad XV$$

wherein $R_{13}$ is lower alkenyl, lower alkynyl or a cyclopropylmethyl group and Z is chlorine, bromine, iodine, or tosyloxy;
or j. converting an ester by re-esterification into an ester of formula I according to known procedures; or k. reacting an acid halide corresponding to an acid of formula XIV with a lower alkanethiol, lower alkenethiol, lower alkynethiol or cyclopropylmethylthiol, after previous conversion of the thiol into an alkali metal or alkaline earth metal salt.

DETAILED DESCRIPTION OF THE INVENTION

As used throughout the specification, the term "lower alkyl" denotes straight or branched chain hydrocarbon groups containing from 1 to 6 carbon atoms such as methyl, ethyl, propyl, isopropyl, pentyl, 3-pentyl and the like. The term "lower alkenyl" and "lower alkynyl" denote straight or branched chain hydrocarbon groups containing from 2 to 6 carbon atoms such as vinyl, allyl, butenyl and pentenyl, ethynyl, propargyl and butynyl. The term "halogen" denotes fluorine, bromine and iodine unless stated otherwise. The term "alkali metal" denotes lithium, sodium, potassium, rubidium and caesium. The term "alkaline earth metal" denotes beryllium, magnesium, calcium, strontium and barium. The term "aryl" denotes mononuclear, polynuclear, substituted or unsubstituted aryl such as phenyl, substituted phenyl, e.g., tolyl, xylyl, mesityl or p-methoxyphenyl or polynuclear aryl groups, e.g., naphthyl, anthryl, phenanthryl, and azulyl. The term "lower alkoxy" denotes those alkoxy groups containing up to 4 carbon atoms e.g., methoxy, ethoxy or isopropoxy. The term "aryloxy" denotes phenoxy groups having one or more substituents such as, alkyl, alkoxy, halogen, dialkylamino and nitro. The term "lower dialkylamino" denotes amino groups having alkyl group substituents each containing up to 4 carbon atoms such as dimethylamino, diethylamino or diisopropylamino and the like.

Preferred polyene compounds of formula I are those in which $R_7$ is an ethyl, isopropyl or propargyl group.

Other preferred polyene compounds of formula I are those in which Y is oxygen and R is a lower alkynyl group.

Also preferred are those polyene compounds of formula I in which $R_1$, $R_2$, $R_3$ and $R_6$ are each methyl or ethyl, $R_4$ and $R_5$ are each hydrogen or methyl, $m$ is 2, $n$ and $p$ are both 1.

Especially preferred polyene compounds of formula I are:

11-Propynyloxy-3,7,11-trimethyl-2,4-dodecadienoic acid cyclopropylmethyl ester,
11-Propynyloxy-3,7,11-trimethyl-2,4-dodecadienoic acid isopropyl ester,
11-Propynyloxy-3,7,11-trimethyl-2,4-dodecadienoic acid ethyl ester,
11-Propynyloxy-3,7,11-trimethyl-2,4-dodecadienoic acid thioethyl ester,
11-Propynyloxy-3,7,11-trimethyl-2,4-dodecadienoic acid propargyl ester,
11-Allyloxy-3,7,11-trimethyl-2,4-dodecadienoic acid isopropyl ester,
11-Allyloxy-3,7,11-trimethyl-2,4-dodecadienoic acid thioethyl ester,
11-Allyloxy-3,7,11-trimethyl-2,4-dodecadienoic acid propargyl ester,
11-Allyloxy-3,7,11-trimethyl-2,4-dodecadienoic acid ethyl ester,
11-Cyclopropylmethoxy-3,7,11-trimethyl-2,4-dodecadienoic acid isopropyl ester,
11-Cyclopropylmethoxy-3,7,11-trimethyl-2,4-dodecadienoic acid thioethyl ester,
11-Cyclopropylmethoxy-3,7,11-trimethyl-2,4-dodecadienoic acid propargyl ester,
11-Propynyloxy-3-methyl-2,4-undecadienoic acid propargyl ester,
10-Propynyloxy-3-methyl-2,4-decadienoic acid propargyl ester,
9-Propynyloxy-3-methyl-2,4-nonadienoic acid propargyl ester,
8-Propynyloxy-3-methyl-2,4-octadienoic acid propargyl ester,
7-Propynyloxy-3,7-dimethyl-2,4-octadienoic acid propargyl ester,
11-Propynyloxy-2,4-undecadienoic acid propargyl ester,
10-Propynyloxy-2,4-decadienoic acid propargyl ester,
9-Propynyloxy-2,4-nonadienoic acid propargyl ester,
8-Propynyloxy-2,4-octadienoic acid propargyl ester and
7-Propynyloxy-7-methyl-2,4-octadienoic acid propargyl ester.

Preferred starting materials which are used in the process in according with the present invention are:

7-Propynyloxy-citronellal,
7-Allyloxy-citronellal,
7-Cyclopropylmethoxy-citronellal,
7-Propynyloxy-1-heptanal,
7-Propynyloxy-1-hexanal,
7-Propynyloxy-1-pentanal,
7-Propynyloxy-1-butanal and
3-propynyloxy-3-methyl-1-butanal.

The phosphine oxides of formulae III and VI can carry lower alkoxy or aryloxy groups. The aryl groups denoted by $R_8$ and $R_9$ can be mononuclear or polynuclear, substituted or unsubstituted aryl, groups.

The phosphoranes of formulae IV and VIII, which can be obtained from the corresponding phosphonium salts, can carry aryl or dialkylamino groups.

In processes (a) and (c) of the present invention, a carbonyl compound of formula II or V is reacted with a phosphine oxide of formula III or VI respectively to give a corresponding polyene compound of formula I. This reaction is carried out in the presence of a base. Preferably, the base is combined with an inert organic solvent. A typical base and solvent combination is sodium hydride with benzene, toluene, dimethylformamide, tetrahydrofuran, dioxane and 1,2-dimetoxyethane. The reaction may also be carried out in the presence of an alkali metal alcoholate in an alcohol, for example, sodium methylate in methanol. The reaction temperature is not critical and may vary between −20°C. and the boiling point of the solvent, preferably at between 0°C. and room temperature. In a particularly preferred embodiment, a carbonyl compound of formula II is reacted with a phosphine oxide of formula III in the presence of 2 moles of sodium hydride in absolute tetrahydrofuran.

In processes (b) and (d) of the present invention, the reaction of a compound of formula II or V with a phosphorane of formula IV or VII respectively, is carried out in the presence of catalytic amounts of an organic acid, preferably acetic acid or benzoic acid, in the presence of a solvent such as benzene, toluene, dimethylformamide, 1,2-dimethoxyethane or dioxane at a temperature between room temperature and the boiling point of the solvent.

In process (e) of the present invention, the reaction of an alcoholate corresponding to formula VIII with a halide or tosylate of formula IX or of an alcoholate of formula IX with a halide or tosylate of formula VIII is carried out in an inert organic solvent, preferably in dimethylformamide, dioxane or hexamethylphosphoric acid triamide. The alcoholate is prepared by reacting an alcohol corresponding to either of formula VIII or IX in the presence of an alkali or alkaline earth metal, preferably in the presence of metallic sodium, sodium hydride or sodium amide. The reaction temperature is not critical and may vary from −20°C. and the boiling point of the reaction mixture. Room temperature is generally preferred, particularly when J in formula IX represents a bromine atom.

In processes (f) and (g) of the present invention, a carbonyl compound of formula II or V is reacted with a compound of formula X or XII respectively to give a compound of formula VI or XIII. For this purpose, a bromo compound corresponding to formula X or XII is dissolved in an inert organic solvent, e.g., benzene, toluene, diethyl ether, dioxane, tetrahydrofuran or a mixture of these solvents, in which is dissolved the carbonyl compound of formula II or V, the mixture obtained is then treated with zinc turnings which have been activated by pretreatment with acid and/or iodine. The resulting organometallic compound of formula X or XII reacts with the carbonyl compound of formula II or V to give an organometallic complex compound. This reaction takes place at a temperature between room temperature and the reflux temperature of the reaction mixture, preferably at the reflux temperature. The organometallic complex is decomposed by the addition of water to give a hydroxy compound of formula XI or XIII. The organic phase is separated, dried and evaporated. The hydroxy compound is dehydrated according to known procedures. A particularly preferred procedure entails treatments of the hydroxy compound with acid, preferably acetic acid, in the presence of sodium acetate and water while warming.

The preparation of polyene compounds of formula I where X is $COOR_7$, comprises esterifying an acid of formula XIV with an alcohol of formula IX in which J represents a hydroxyl group. For this purpose, an acid of formula XIV is converted into its corresponding acid halide by reacting said acid with a halogenating agent. Typical halogenating agents that may be used are: thionyl chloride, phosphorus trichloride, thionyl bromide or phosphorus oxychloride, preferably thionyl chloride. The reactions conducted in an inert solvent such as, petroleum ether, benzene, hexane etc. to which an acid binding agent, e.g., pyridine, triethylamine, quinoline etc., preferably pyridine has been added. The acid halide is subsequently reacted with the desired alcohol in an inert solvent, e.g., benzene, toluene, hexane, isooctane, chloroform, carbon tetrachloride or ethyleneglycol dimethyl ether in the presence of an acid binding agent (previously mentioned) to give the desired ester. Further, an acid of formula XIV can be esterified with a lower alkyl, lower alkenyl or lower alkynyl halide, preferably the bromide, in the presence of a base.

A polyene compound of formula I in which Y is oxygen or sulphur and R is hydrogen, can be etherified with a compound of formula XV. This etherification is carried out in the same manner as previously described for the reaction of a compound of formula VIII with a compound of formula IX in which J represents a chlorine, bromine or iodine atom or the tosyloxy group.

After conversion into a corresponding halocarbonyl compound, an acid of formula XIV can be converted into a polyene compound of formula I in which X represents the group $-COSR_7$ by treament with a lower alkanethiol, lower alkenethiol, lower alkynethiol or cyclopropylmethylthiol.

An ester of formula I can be obtained by the reesterification of an ester prepared from an acid of formula XIV by known procedures.

The starting materials of formulae II, V, III and XIV can be prepared by reacting a corresponding terminally unsaturated compound of the formulae:

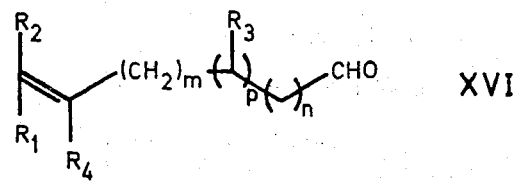

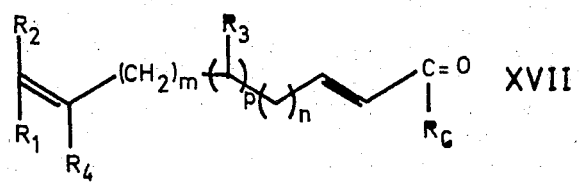

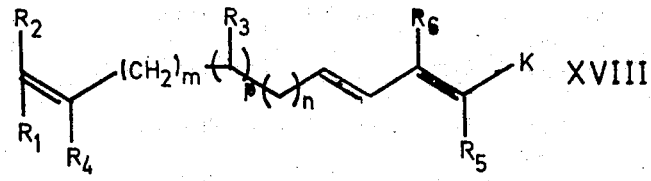

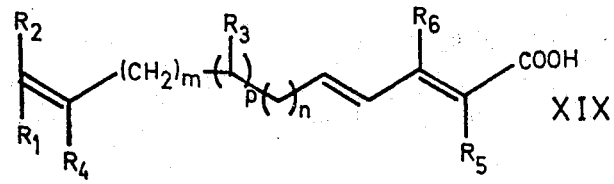

in which formulae $R_1$, $R_2$, $R_3$, $R_4$, $R_5$, $R_6$, $m$, $p$, $n$ and K are as previously defined;
with water.

This reaction is carried out in the presence of an acid, preferably a mineral acid such as, sulphuric acid. The reaction is conducted in an inert organic solvent, preferably tetrahydrofuran. The reaction can be carried out at a temperature between 0°C. and the reflux temperature of the reaction mixture, preferably between 0°C. and 40°C. There are obtained compounds of formulae II, V, VIII and XIV in which Y is oxygen and R is hydrogen. A preferred process is that described in J. Amer, Chem. Soc. 91, 5646 (1969). This process consists in reacting such a terminally unsaturated compound with water and a mercuric salt and subsequently reducing the mercury-containing intermediate without isolation thereof. Suitable mercuric salts are mercuric acetate and other acylates, mercuric nitrate, meruric trifluoroacetate and mercuric halides. Suitable reducing agents are alkali metal borohydrides, hydrazine and sodium amalgam.

Where a terminally unsaturated compound of formula XVI or XVII is used, the aldehyde function is protected by means of an amine, (cf J. Org. Chem. 39, 108 (1974), prior to the addition of water to the terminal double bond.

Where a compound of formulae II, IV or XIV in which Y is sulphur and R is hydrogen is desired, then a terminally unsaturated compound of formula XVI, XVII or XIX is treated with a hydrohalic acid, preferably hydrochloric acid or hydrobromic acid. Here also, the aldehyde function is protected prior to the hydrohalic acid addition. The protection can be effected by means of an amine or by acetal formation with a lower alkanol, preferably methanol, according to known procedures.

The reaction of a terminally unsaturated compound of formula XVI, XVII or XIX with a hydrohalic acid is carried out in an inert organic solvent such as, ether, hexane, methylene chloride, chloroform or carbon tetrachloride. The reaction mixture is evaporated and the residue taken up in ether. The ether solution is then washed with a saturated sodium bicarbonate solution, dried over sodium sulphate and re-evaporated. The reaction product is usually obtained in pure form. It can, if necessary, be further purified by chromatography on silica gel.

The resulting halo compound carrying a protected aldehyde function is converted into an isothiouronium salt with thiourea as described in J. Org. Chem. 27, 93 (1962). This isothio-uronium salt is cleaved with a high boiling amine to give the desired thiol compound of formulae II, V or XIV where Y is sulphur and R is hydrogen. The thiol compound corresponding to formula XIV by reduction with lithium aluminum hydride and, if desired, subsequent halogenation with a phosphorus trihalide. The thus obtained thiol acetals or ketals are cleaved in the usual manner with dilute acid, preferably aqueous hydrochloric acid.

The terminally unsaturated compounds of formulae XVII, XVIII and XIX can be obtained from the terminally unsaturated compounds of formula XVI according to the following formula schemes I and II according to known procedures (See Belgian Pat. No. 800,948):

Formula Scheme I

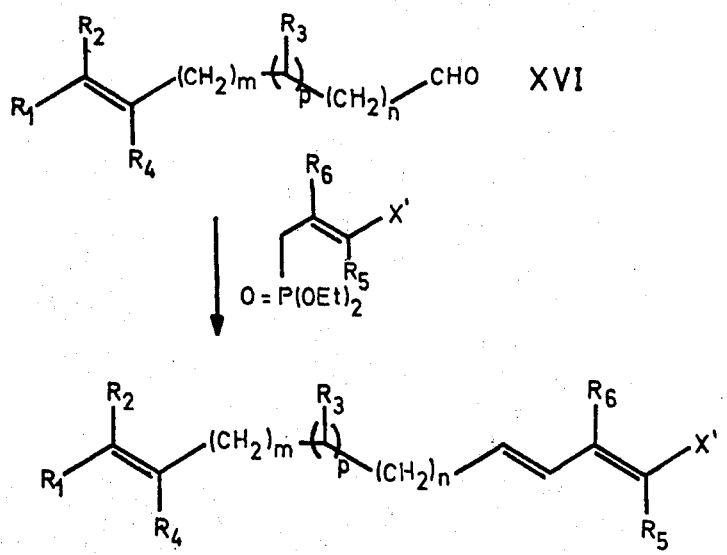

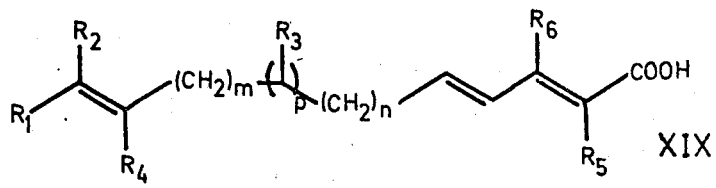
XIX
1) LiAlH₄
2) PX₃
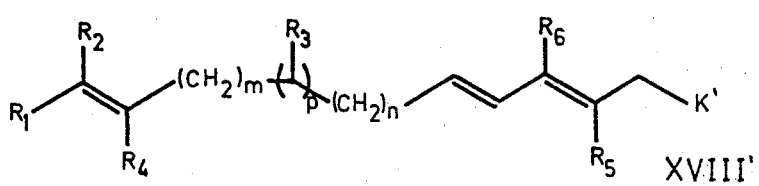
XVIII'
K' = OH, Halogen
Formula Scheme II
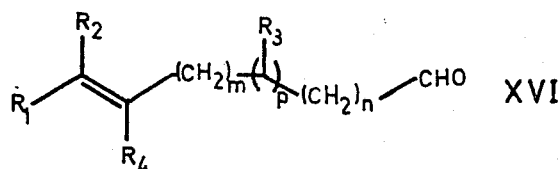  XVI
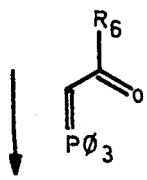
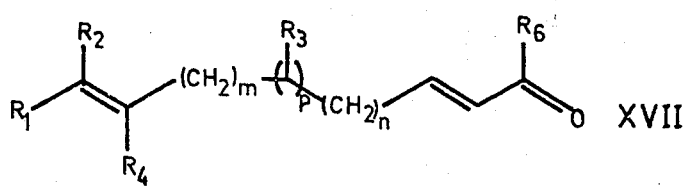  XVII
The terminally unsaturated compounds of formula XVI are known. They can be obtained from aldehydes of the formula:

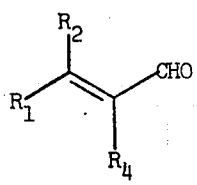   XX
wherein R, $R_2$ and $R_4$ are as previously defined.
/From the following scheme III, it will be seen that all compounds of formula XVI can be obtained by either of reaction sequences A or B, described hereinafter.
Formula Scheme III
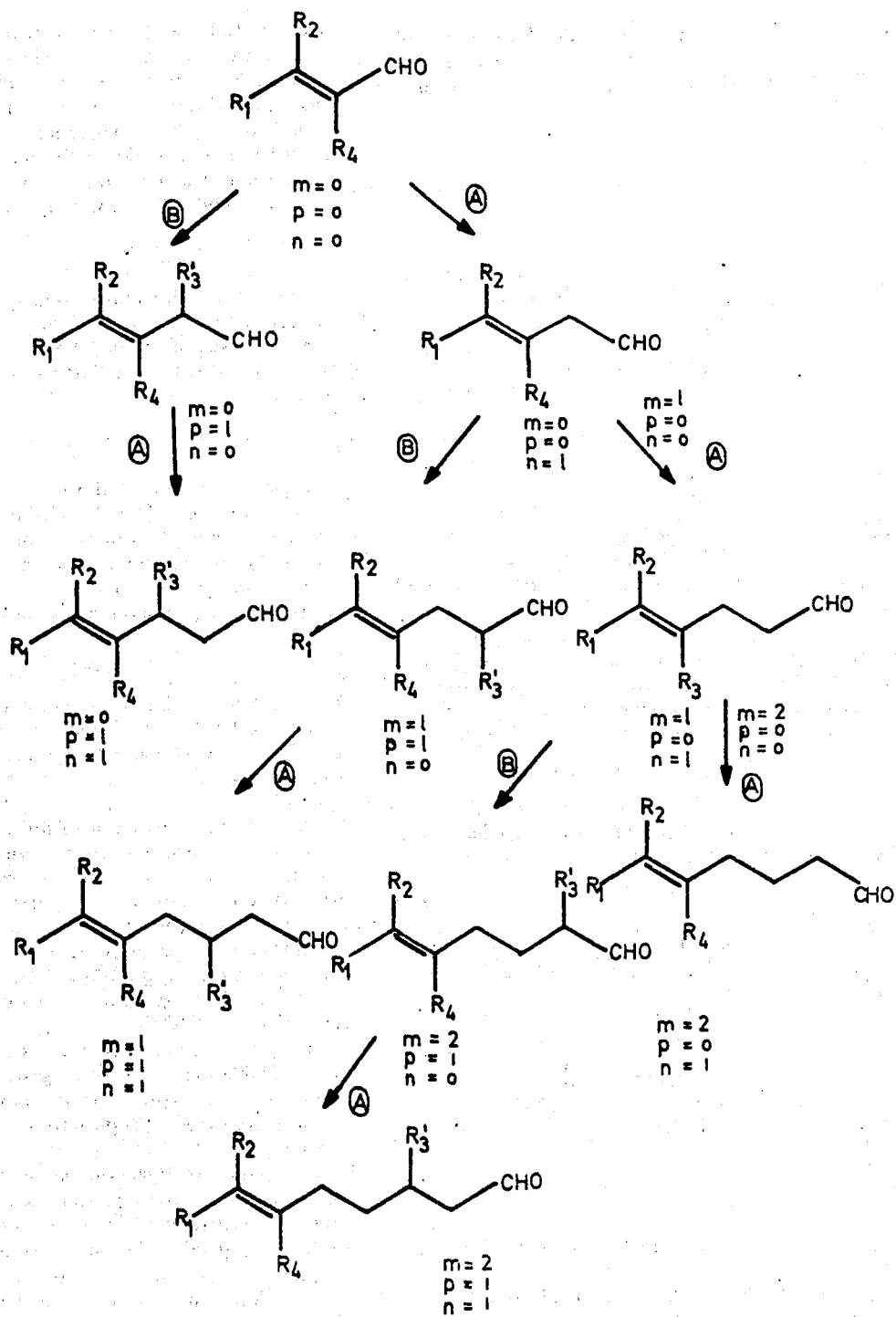

Reaction type A

In reaction type A, an aldehyde in accordance with formula scheme III is reacted with dimethylsulphonium-methylide of the formula:

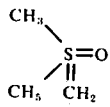  XXI in a mixture of dimethyl sulphoxide and tetrahydrofuran at about 0°C. [see Corey, J. Amer. Chem. Soc. 87, 1353 (19650]. There is obtained an epoxide of the formula:

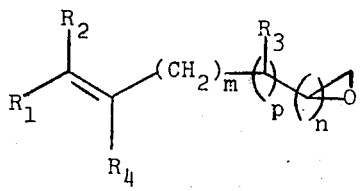  XXII wherein $R_1$, $R_2$, $R_3$, $R_4$, $m$, $p$ and $n$ are as previously defined.

Such an epoxide is converted into the desired compound of formula XVI by rearrangement with boron trifluoride etherate or preferably by treatment with anhydrous magnesium bromide in ether at a temperature below 0°C., preferably at −70°C. to −10°C.

Reaction type B

In reaction type B, an aldehyde in accordance with formula scheme III is reacted with a Grignard compound of the formula:

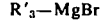  XXIII wherein $R'_3$ is lower alkyl to give an alcohol of the formula:

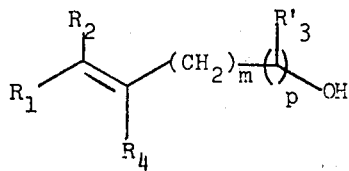  XXIV wherein $R_1$, $R_2$, $R_3$, $R_4$, $m$ and $p$ are as previously defined.

An alcohol of formula XXIV is oxidized with chromium trioxide in acetone in the presence of sulphuric acid, preferably at a temperature between 0°C. and room temperature, to give a ketone of the formula:

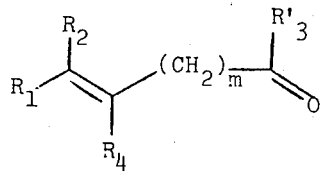  XXV wherein $R_1$, $R_2$, $R'_3$, $R_4$ and $m$ are as previously defined. The desired aldehyde is obtained from a ketone of formula XXV by reaction with dimethylsulphonium-methylide of formula XXI and subsequent rearrangement with anhydrous magnesium bromide as previously described in connection with reaction type A.

Especially valuable starting materials of formula II are compounds of the formula:

  R—O—(CH₂)_q—CHO    XXVI wherein R is as previously defined and $q$ represents an integer of from 2 to 6 inclusive.

An aldehyde of formula XXVI is obtained by etherifying one of the hydroxyl groups in a compound of the formula:

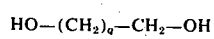  HO—(CH₂)_q—CH₂—OH    XXVII wherein $q$ is as defined above;
with a lower alkenyl halide, a lower alkynyl halide or a cyclopropylmethyl halide in the manner described previously for the reaction of a compound of formula VIII with a compound of formula IX.

The resulting compounds of the formula:

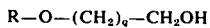  R—O—(CH₂)_q—CH₂OH    XXVIII wherein R and $q$ are as previously defined;
can be oxidized, for example with chromium trioxide/pyridine in methylene chloride, preferably at between 0°C. and room temperature, to give compounds of formula XXVI.

The polyene compounds of formula I occur as cis-/trans isomer mixtures. The mixtures can be separated into their isomeric forms by adsorption on a material with selective activity. The isomeric mixture is dissolved in an inert organic solvent such as hexane, ether or ethyl acetate and adsorbed on silica gel. The isomers adsorbed in different zones can be eluted with one of the previously mentioned solvents or mixtures thereof and isolated.

The isomeric mixtures can also be separated by fractional distillation, preparative gas chromatography or preparative thin layer chromatography.

The polyene compounds of formula I was suitable for combatting pests. In contrast to most of the hitherto known pesticides which kill, paralyze or drive away the pests as contact- and feed-poisons, the polyene compounds of formula I interfere with the hormonal system of the pest organism. In insects, for example, the metamorphosis to the imago, the laying of viable eggs and the development of laid normal eggs was disturbed. The sequence of generations is interrupted and the insects are indirectly killed. The polyene compounds of formula I are practically non-poisonous to vertebrates.

The toxicity of the polyene compounds of formula I lies at over 1000 mg/kg body weight. The present polyene compounds are, moreover, readily degraded. The danger of an accumulation is therefore excluded. The polyene compounds of formula I can accordingly be employed for combatting pests in animals, plants and foodstuffs.

The polyene compounds of formula I are especially suitable for combatting invertebrate pests, particularly Arthropoda and Nematoda and more particularly Acarina, Orthoptera, Blattidae, Psocoids, Thysanopteroids, Hemiptera, Hymenoptera, Choleoptera, Diptera, Lepidoptera and Neuroptera such as,

| | |
|---|---|
| Metatetranychus | (red citrus spider mite) |
| Tetranychus spp. | (common spider mite) |
| Anthonomus grandis | (boll weevil) |
| Chilo suppressalis | (Asiatic rice-borer) |
| Diatraea saccharalis | |
| Heliothis spp. | (bollworm) |
| Pyrausta nubilalis | (corn borer) |
| Carpocapsa pomonella | (codlin moth) |
| Ceratitis capitata | (Mediterranean fruit fly) |
| Aonidiella aurantii | (red Californian scale louse) |
| Aphis gossypii | (cotton aphid) |
| Myzus persicae | (peach aphid) |
| Locusta migratoria | (migratory locust) |
| Tribolium spp. | (rice flour beetle) |
| Sitophilus spp. | (grain weevil) |
| Ephestia kuhniella | (flour moth) |
| Plodia interpunctella | (dried-fruit moth) |
| Aedes spp. | (mosquitoes) |
| Anopheles spp. | (malarial mosquito) |
| Culex spp. | (house mosquito) |
| Musca domestica | (housefly) |
| Stomoxys calcitrans | (stable fly [calf biter]) |
| Blattella germanica | (cockroach) |
| Cochliomyia hominivorax | (screw-worm) |

The polyene compounds of formula I are especially suitable for combatting flies and mosquitoes, especially for Diptera such as Culicidae.

As will be evident from the following, a concentration of polyene compounds of formula I of $10^{-3}$ to $10^{-6}$ g/cm$^2$ is generally sufficient to guarantee the desired effect.

The polyene compounds of formula I can be used as pesticides in the form of concentrates, granulates or, together with carriers, in the form of sprays, aerosols or powders. For certain purposes, it can be advantageous to use emulsions, suspensions or solutions which contain emulsifiers or wetting agents. As solid carrier materials there may be mentioned, for example, chalk, talc, bentonite, kaolin, diatomaceous earth, siliceous earth, Fuller's earth, lime, gypsum, powders and dusts from organic waste products etc.

In general, the polyene compounds of formula I can be formulated as pesticides according to the procedures described, for example, in, Farm Chemicals, Volume 128, page 52 et seq. The pesticides can also contain other additives such as emulsifiers or masking agents.

The pesticides provided by this invention can be made up in the form of concentrates which are suitable for storage and transport. Such concentrates can contain, for example, 40–70% of a polyene compound of formula I. These concentrates can be diluted with the same or a different carrier material to provide concentrations which are suitable for practical use. In a ready-for-use pesticide in a form for spraying there can be present, for example, a concentration of 0.01–0.5%, preferably 0.1%, of a polyene compound of formula I. The concentrations can, however, also be smaller or larger.

Polyene compounds of formula I give the following results in the Aedes larvicide and Aedes morphogenetic tests:

1. Aedes larvicide test

20 μl of an acetone solution of polyene compounds of formula I in an defined concentration are mixed with 2 ml water [tap water: distilled water (1:1)]. 10 freshly hatched first instar larvae are added to the treated water which is present in test tubes. The temperature is 25°C. and the relative air humidity is 60%. The test tubes contain small amounts of hamster food. Untreated water and water treated with acetone serve as controls. The results are given in Table 1.

Table 1

| Polyene compound | Dose ($10^{-x}$) g/ml water | % Reduction of larvae 4 days after start in % |
|---|---|---|
| Isopropyl 3,7,11-trimethyl-11-(2-propynyloxy)-2,4-dodecadienoate | 5 | 100 |
| S-Ethyl 3,7,11-trimethyl-11-(2-propynyloxy)-2,4-dodecadienoate | 5 | 100 |

2. Aedes test (morphogenetic)

0.2 ml. of an acetone solution of polyene compound of formula I in a defined concentration are mixed with 20 ml. of tap water. 10 last instar larvae, are added to the treated water and kept in test tubes at 25°C. and 60% relative air humidity until the adult animals are hatched. The test tubes contain small pieces of dog biscuit and are sealed with a cotton plug. Untreated water (UC) and water treated with acetone (AC) serve as controls. The results are expressed as % reduction of adult animals in comparison to the controls. The counting is effected after 14 to 21 days.

Calculation:

$$\frac{\% \text{ adult animals } (UC + ACO) - \% \text{ adult animals (treated)}}{100 - \% \text{ adult animals (treated)}} \times 100 = \%$$

The results are given in Table 2.

Table 2

| Polyene compound | Dose ($10^{-x}$) g/ml water | % Reduction of adults in % |
|---|---|---|
| Isopropyl 3,7,11-trimethyl-11-(2-propynyloxy)-2,4-dodecadienoate | 8 | 100 |
| S-Ethyl 3,7,11-trimethyl-11-(2-propynyloxy)-2,4-dodecadienoate | 8 | 97 |

The pesticides provided by the present invention can be used against pests according to the customary methods such as, by contact or intake with food.

The following non-limiting examples are provided to illustrate the process provided by the present invention.

19

All temperatures are in degrees Centigrade. The ether used is diethyl ether.

EXAMPLE 1

5.8 g. of 1-carbethoxy-2-methyl-1-propenyl-diethylphosphonate and 4.2 g. of 7-propynyloxy-citronellal are dissolved in 50 ml. of N,N-dimethylformamide and treated dropwise, while cooling with ice, with a solution of 0.51 g. of sodium in 10 ml. of absolute alcohol. Subsequently, the mixture is left to stir for 2 hours at room temperature. The mixture is poured on to an ice-cold sodium chloride solution and extracted three times with hexane/ether (1:1). The extracts are washed with water and saturated sodium chloride solution, dried over sodium sulphate and evaporated. By chromatography on silica gel using hexane/ethyl acetate (19:1), there is obtained pure 3,7,11-trimethyl-11-(2-propynyloxy)-2,4-dodecadienoic acid ethyl ester which distils in a bulb-tube at 113°C/0.02 mmHg; $n_D^{25}$ = 1.4970.

EXAMPLE 2

The starting material of Example 1 can be prepared as follows: 172.2 g. of hydroxycitronellal and 106.1 g. of orthoformic acid methyl ester are treated dropwise, while cooling with ice, with a solution of 0.5 g. of p-toluenesulphonic acid in 800 ml. of absolute methanol. After 2 hours, 5 g. of sodium acetate are added and the mixture is concentrated on a rotary evaporator at 50°C. Upon distillation, the residue yields pure 1,1-dimethoxy-3,7-dimethyl-7-octanol; boiling point = 102°C/0.4 mmHg; $n_D^{22}$ = 1.4400.

59 g. of sodium amide (50% suspension in benzene) are placed in 1 liter of 1,2-dimethoxyethane and treated dropwise, while cooling with ice, with 109.2 g. of 1,1-dimethoxy-3,7-dimethyl-7-octanol in 400 ml. of 1,2-dimethoxyethane. The mixture is left to stir under a nitrogen atmosphere for 15 hours at 85°C. The mixture is then again cooled and treated dropwise with a solution of 89.3 g. of propargyl bromide in 250 ml. of 1,2-dimethoxyethane. The mixture is then left to stir at 40°C. until the reaction is complete. The mixture is poured on to 4 liters of ice-water and extracted twice with 2.5 liters of ether. The extracts are washed with 10% sodium hydroxide, water and saturated sodium chloride solution, dried over sodium sulphate and evaporated. By distillation or chromatography, there is obtained pure dimethylacetal of 3,7-dimethyl-(2-propynyloxy)-octanal; boiling point (bulb-tube) = 70°C/0.03 mmHg; $n_D^{25}$ = 1.4491. 65 g. of the dimethylacetal of 3,7-dimethyl-7-(2-propynyloxy)-octanal are heated at 40°C. for 16 hours with a mixture of 300 ml. of 2-N hydrochloric acid, 700 ml. of water and 1 liter of tetrahydrofuran while stirring well. For the working up, the mixture is poured on to 1 liter of ice-water and extracted twice with 1.5 liters of ether. The extracts are washed with 10% sodium carbonate solution, water and saturated sodium chloride solution, dried over sodium sulphate and evaporated. By distillation, there is obtained pure 3,7-dimethyl-7-(2-propynyloxy)-octanal; boiling point = 113°C/1 mmHg; $n_D^{25}$ = 1.4553.

EXAMPLE 3

2.63 g. of 3,7,11-trimethyl-11-(2-propynyloxy)-2,4-dodecadienoic acid are dissolved in 40 ml. of methyl ethyl ketone and then treated with 2.45 g. of potassium carbonate and 6.1 g. of isopropyl iodide. The mixture is heated at reflux under a nitrogen atmosphere for 6 hours, then poured on to ice-water and extracted with ether. The extracts are washed with water and saturated sodium chloride solution, dried and evaporated. By chromatography on silica gel, there is obtained pure 3,7,11-trimethyl-11-(2-propynyloxy)-2,4-dodecadienoic acid isopropyl ester; boiling point (bulb-tube) = 122°C/0.023 mmHg; $n_D^{25}$ = 1.4940.

EXAMPLE 4

Following the procedure of example 3, but using propargyl bromide there is obtained 3,7,11-trimethyl-11-(2-propynyloxy)-2,4-dodecadienoic acid propargyl ester; boiling point (bulb-tube) = 119°C/0.02 mmHg; $n_D^{21}$ = 1.5100.

EXAMPLE 5

The starting material of Examples 3 and 4 may be prepared as follows:

13.2 g. of 3,7,11-trimethyl-11-(2-propynyloxy)-2,4-dodecadienoic acid ethyl ester are treated, while cooling with ice, with 120 ml. of methanol, 60 ml. of tetrahydrofuran and 15 g. of potassium hydroxide in 60 ml. of water. The mixture is left to stir under a nitrogen atmosphere for 1 day at room temperature and then for 2 hours at 40°C. The mixture is concentrated on a rotary evaporator, the residue poured on to ice-water and adjusted to pH 3 with 2-N hydrochloric acid. The mixture is then extracted three times with ether, the extracts are washed with saturated sodium chloride solution, dried and evaporated. The crude 2,7,11-trimethyl-11-(2-propynyloxy)-2,4-dodecadienoic acid was used without further purification.

EXAMPLE 6

2.63 g. of 3,7,11-trimethyl-11-(2-propynyloxy)-2,4-dodecadienoic acid are dissolved in 45 ml. of benzene and treated with 1.25 g. of oxalyl chloride. After 3 hours, 1 ml. of ethyl mercaptan is added while cooling with ice, whereupon the mixture is left to react at room temperature for 16 hours. For the working up, the mixture is poured on to ice-cold 10% potassium bicarbonate solution and extracted three times with ether. The extracts are washed with water and saturated sodium chloride solution, dried and evaporated. By chromatography on silica gel with hxane/ether (19:1), there is obtained pure 3,7,11-trimethyl-11-(2-propynyloxy)-2,4-dodecadienoic acid thioethyl ester; $n_D^{22}$ = 1.5281.

EXAMPLE 7

Following the procedure of Example 1, but using 7-allyloxy-citronellal there is obtained 3,7,11-trimethyl-11-allyloxy-2,4-dodecadienoic acid ethyl ester; $n_D^{24}$ = 1.4902.

EXAMPLE 8

The starting material of Example 7 can be prepared as follows:

Following the procedure of Example 1, there is obtained from 1,1-dimethoxy-3,7-dimethyl-7-octanol and allyl bromide th dimethyl acetal of 3,7-dimethyl-7-allyloxy-octanal; boiling point = 80°C/0.03 mmHg. By subjecting this dimethyl acetal to the hydrolysis procedure described in Example 1 there is obtained 7-allyloxy-citronellal which is used for the Horner reaction without further purification.

EXAMPLE 9

Following the procedure of Example 3, there is obtained from 3,7,11-trimethyl-11-allyloxy-2,4-dodecadienoic acid using isopropyl iodide the 3,7,11-trimethyl-11-allyloxy-2,4-dodecadienoic acid isopropyl ester; $n_D^{24} = 1.4865$.

EXAMPLE 10

Following the procedure of Example 9 but using propargyl bromide there is obtained 3,7,11-trimethyl-11-allyloxy-2,4-dodecadienoic acid propargyl ester; $n_D^{24} = 1.5018$.

The 3,7,11-trimethyl-11-allyloxy-2,4-dodecadienoic acid used as the starting material in Examples 9 and 10 is prepared from the corresponding ethyl ester in a manner analogous to that described in Example 3.

EXAMPLE 11

Following the procedure of Example 6, from 3,7,11-trimethyl-11-(2-propynyloxy)-2,4-dodecadienoic acid and cyclopropylmethyl alcohol there is obtained 3,7,11-trimethyl-11-(2-propynyloxy)-2,4-dodecadienoic acid cyclopropylmethyl ester.

EXAMPLE 12

Following the procedure of Example 6, from 3,7,11-trimethyl-11-allyloxy-2,4-dodecadienoic acid there is obtained 3,7,11-trimethyl-11-allyloxy-2,4-dodecadienoic acid thioethyl ester; $n_D^{23} = 1.5280$.

EXAMPLE 13

Following the procedure of Example 1, there is obtained using 6-propynyloxy-1-hexanal the 3-methyl-10-(2-propynyloxy)-2,4-decadienoic acid ethyl ester; boiling point (bulb-tube) = 123°C/0.03 mmHg; $n_D^{26} = 1.5000$.

EXAMPLE 14

The starting material of Example 13 can be prepared as follows:

118 g. of 1,6-hexanediol are introduced into 800 ml. of absolute tetrahydrofuran and, while stirring well, treated portionwise over a period of 4 hours with 30 g. of sodium hydride. 60 ml. of hexamethylphosphoric acid triamide are then added, the mixture is heated to reflux and treated over a period of 12 hours with a solution of 149 g. of propargyl bromide and 200 ml. of tetrahydrofuran. The cooled mixture is poured on to ice-water and extracted three times with ether. The ether solutions are washed with water and sodium chloride solution, dried over sodium sulphate and evaporated. By distillation or chromatography there is obtained pure 6-(2-propynyloxy)-1-hexanol; boiling point (bulb-tube) = 75°C/0.015 mmHg; $n_D^{25} = 1.4560$.

A solution of 298 g. of pyridine and 3.1 liters of dry methylene chloride is treated within 5 minutes with 188 g. of chromium trioxide with intensive stirring and cooling with an ice-bath. The ice-bath is then removed and 48.5 g. of 6-(2-propynyloxy)-1-hexanol are added at room temperature while stirring. After 15 minutes, the mixture is poured on to ice-water and extracted twice with ether. The ether extracts are washed successively with 5% sodium hydroxide solution, 5% hydrochloric acid, 10% potassium bicarbonate solution and saturated sodium chloride solution, dried over sodium sulphate and evaporated. By chromatography on silica gel using hexane/ethyl acetate (4:1) there is obtained pure 6-(2-propynyloxy)-1-hexanal.

EXAMPLE 15

In a manner analogous to that described in Example 3, there is obtained from 3-methyl-10-(2-propynyloxy)-2,4-decadienoic acid using propargyl bromide.

3-methyl-10-(2-propynyloxy)-2,4-decadienoic acid propargyl ester; boiling point (bulb-tube) = 127°C/0.03 mmHg; $n_D^{26} = 1.5151$.

EXAMPLE 16

Following the procedure of Example 15, but using isopropyl iodide there is obtained 3-methyl-10-(2-propynyloxy)-2,4-decadienoic acid isopropyl ester; $n_D^{22} = 1.4988$.

3-methyl-10-(2-propynyloxy)-2,4-decadienoic acid used as the starting material is prepared from the corresponding ethyl ester in a manner analogous to that described in Example 3.

The following example illustrates a typical pesticide composition containing one of the polyene compounds provided by the present invention:

EXAMPLE 17

500 g. of isopropyl 3,7,11-trimethyl-11-(2-propynyloxy)-2,4-dodecadienoate are mixed with 100 g. of a mixture of a condensation product of alkylphenol and ethylene oxide and a salt of an alkyl-arylsulphonic acid (Atlox 2081 B., Atlas Chemie, 43 Essen, Germany). The mixture is made up to 1000 ml. with tri(n-alkyl)benzenes ("SNA", Chemische Werke Hüls AG. 4370 Marl, Germany; aromatic content 99.5%; boiling range 187°–213°C.). The concentrate is brought to the desired dilution with water before use and sprayed on the areas to be protected.

We claim:

1. A polyene compound of the formula:

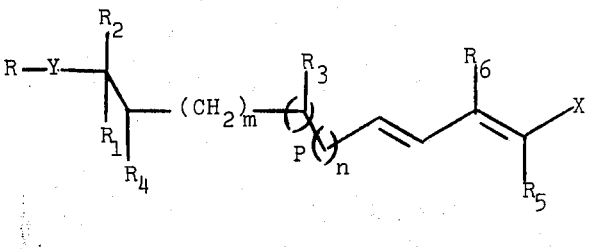

wherein R is lower alkenyl, lower alkynyl or a cyclopropylmethyl group, $R_1$, $R_2$, $R_3$ and $R_6$ are each hydrogen or a lower alkyl group, $R_4$ and $R_5$ are each hydrogen or methyl, Y is oxygen; X is —$COOR_7$, wherein $R_7$ is lower alkyl; $n$ and $p$ may be zero or 1 and $m$ is an integer from zero to 2 inclusive.

2. A compound according to claim 1 wherein $R_7$ is selected from the group consisting of methyl, ethyl, 3-pentyl; $R_4$ and $R_5$ are each hydrogen, Y is oxygen and R is propargyl, allyl and cyclopropylmethyl.

3. A compound according to claim 1 wherein $R_4$ is methyl and $R_5$ is hydrogen or methyl.

4. A compound according to claim 1 wherein said compound is 11-propynyloxy-3,7,11-trimethyl-2,4-dodecadienoic acid, isopropyl ester.

5. A compound according to claim 2 wherein said compound is 11-propynyloxy-3,7,11-trimethyl-2,4-dodecadienoic acid, ethyl ester.

6. A compound according to claim 2 wherein said compound is 11-allyloxy-3,7,11-trimethyl-2,4-dodecadienoic acid, isopropyl ester.

7. A compound according to claim 2 wherein said compound is 11-allyloxy-3,7,11-trimethyl-2,4-dodecadienoic acid, ethyl ester.

8. A compound according to claim 2 wherein said compound is 11-cyclopropylmethoxy-3,7,11-trimethyl-2,4-dodecadienoic acid, isopropyl ester.

9. An insecticidal composition containing as an essential active ingredient a metamorphosis inhibiting amount of a polyene compound of the formula:

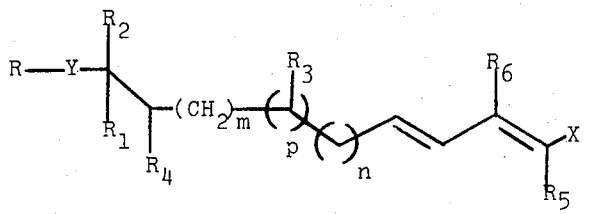

wherein R is lower alkenyl, lower alkynyl or a cyclopropylmethyl group, $R_1$, $R_2$, $R_3$ and $R_6$ are each hydrogen or a lower alkyl group, $R_4$ and $R_5$ are each hydrogen or methyl, Y is oxygen; X is —COOR$_7$, wherein $R_7$ is lower alkyl; n and p may be zero or 1 and m is an integer from zero to 2 inclusive;
in association with a compatible carrier material.

10. An insecticidal composition according to claim 9 wherein said polyene compound is 11-propynyloxy-3,7,11-trimethyl-2,4-dodecadienoic acid, isopropyl ester.

11. An insecticidal composition according to claim 9 wherein said polyene compound is 11-propynyloxy-3,7,11-trimethyl-2,4-dodecadienoic acid, ethyl ester.

12. An insecticidal composition according to claim 9 wherein said polyene compound is 11-allyloxy-3,7,11-trimethyl-2,4-dodecadienoic acid, isopropyl ester.

13. An insecticidal composition according to claim 9 wherein said polyene compound is 11-allyloxy-3,7,11-trimethyl-2,4-dodecadienoic acid, ethyl ester.

14. An insecticidal composition according to claim 9 wherein said polyene compound is 11-cyclopropylmethoxy-3,7,11-trimethyl-2,4-dodecadienoic acid, isopropyl ester.

15. A process for protecting materials from insect pests which comprises applying to said materials an effective amount of a metamorphosis inhibiting composition containing a polyene compound of the formula:

wherein R is lower alkenyl, lower alkynyl or a cyclopropylmethyl group, $R_1$, $R_2$, $R_3$ and $R_6$ are each hydrogen or a lower alkyl group, $R_4$ and $R_5$ are each hydrogen or methyl, Y is oxygen; X is —COOR$_7$, wherein $R_7$ is lower alkyl; n and p may be zero or 1 and m is an integer from zero to 2 inclusive and a compatible carrier.

16. The process of claim 15 wherein said material is a foodstuff, animal, or plant.

* * * * *